United States Patent [19]

May et al.

[11] Patent Number: 4,722,940

[45] Date of Patent: Feb. 2, 1988

[54] AMINOALKYL PHENYL SELENIDES FOR THE TREATMENT OF HYPERTENSION AND NERVOUS SYSTEM DYSFUNCTIONS

[75] Inventors: Sheldon W. May, Atlanta; Heath H. Herman, Chamblee; Steven F. Roberts, Atlanta, all of Ga.

[73] Assignee: Georgia Tech Research Corporation, Atlanta, Ga.

[21] Appl. No.: 816,909

[22] Filed: Jan. 8, 1986

Related U.S. Application Data

[62] Division of Ser. No. 643,556, Aug. 23, 1984, Pat. No. 4,529,870.

[51] Int. Cl.$^4$ ............................................. A61K 31/095
[52] U.S. Cl. .................................................... 514/706
[58] Field of Search .......................................... 514/706

[56] References Cited

U.S. PATENT DOCUMENTS

4,415,591 11/1983 May et al. ............................ 424/330

OTHER PUBLICATIONS

Bey et al., "Further Studies on the Inhibition of Monoamine Synthesis by Monoflouromethyldopa," Br. J. Pharmac., (1980), vol. 70, 571–576.

Judy et al., "Sympathetic Nerve Activity, Role in Regulation of Blood Pressure and Spontaneously Hypertensive Rat," Supp. II, Cir. Res., vol. 38, No. 6, Jun. 1976, 21–29.

Reich, "Organoselenium Oxidations", (1978), *Oxidation in Organic Chemistry, Part C.*, Chapter 1, 1–130.

Lau, "Arylthio (or seleno, or sulfonyl) methyl-substituted phenolic compounds as photographic Couplers," 25–Noncondensed Aromatics, vol. 80, 351, (1974).

J. Heck et al., Chem. Abst. 96: 162,393q (1982).

S. Murahashi, J.A.C.S. 102(7): 2456–2458 (1980)–"Novel Transformation of Primary, Secondary and Tertiary Amines to Organo Selenides with Ruthenium Catalyst".

D. Seebach et al., Chem. Abstracts 87: 117652(b), (1977).

H. Reich et al., J. Org. Chem. 44(18): 3148–51 (1979)–Organoselenium Chemistry Dealkylation of Amines with Benzeneselenol.

*Primary Examiner*—Douglas W. Robinson
*Attorney, Agent, or Firm*—Newton, Hopkins & Ormsby

[57] ABSTRACT

The preparation of aminoalkyl phenyl selenides and pharmaceutically acceptable salts thereof is disclosed which are useful for the treatment of hypertension and related vascular diseases and the treatment of nervous system dysfunctions.

5 Claims, No Drawings

AMINOALKYL PHENYL SELENIDES FOR THE TREATMENT OF HYPERTENSION AND NERVOUS SYSTEM DYSFUNCTIONS

BACKGROUND OF THE INVENTION

This is a continuation of co-pending application Ser. No. 643,556 filed on Aug. 23, 1984, now U.S. Pat. No. 4,579,870 issued April 1986.

1. Field of the Invention

This invention relates to the synthesis of aminoalkyl phenyl selenides useful for the treatment of hypertension and nervous system dysfunctions.

2. Description of the Prior Art

Phenolic aryl-seleno and aryl-thio compounds and other selenide and sulfide derivatives have been disclosed for use as photographic couplers. Lau, Phillip T. S., Arylthio (or seleno, or sulfonyl) Methyl-Substituted Phenolic Compounds As Photographic Couplers, Chem. Abstracts 80:82391. Neither the structures, nor the use disclosed by Lau are related to the compositions of the present invention.

May et al., U.S. Pat. No. 4,415,591 of Nov. 15, 1983, which patent is assigned in common herewith, the subject matter of which is incorporated herein by reference, discloses a method for treating hypertension involving the administration of aminoalkyl phenyl sulfide derivatives; there is also disclosed a method for evaluating the hypotensive potential of these compounds through the rate of enzymatic oxygenation by dopamine-beta-hydroxylase in the presence of an electron donor such as hexacyanoferrate (II) or ascorbic acid; and pharmaceutical compositions are also disclosed which comprise aminoalkyl phenyl sulfide or a salt thereof in amount effective for treatment of hypertension, a monoamine oxidase inhibitor and a nontoxic excipient.

As compared with the May et al. patent, this invention involves specifically different pharmaceutical compounds namely, aminoalkyl phenyl selenides and the salts thereof, which have been found not only to cause substantial systemic blood pressure reduction, but may also provide potent clinical benefits with respect to nervous system dysfunctions and, in particular due to the unusual electrochemical properties of the selenoxide compound produced by the enzymatic oxygenation of the selenide, to enable reversible inhibition of the function of adrenergic neurons. This reversible inhibition is due to depletion of intracellular ascorbate, as more fully described below in the Detailed Description of the Invention and Preferred Embodiments.

While organosulfur chemistry is paralleled in a number of aspects by organoselenium chemistry, the facility of oxidation and reduction reactions can differ greatly. Riech, H. J. (1978), Oxidation in Organic Chemistry (Trahanovsky, W. ed.), Part C. pp 1–129, Academic Press, London and New York. For example, it has been reported that the monooxygenase activity of Aspergillus niger does not produce selenoxides from selenide substrates, despite the ready sulfoxidation of sulfides under the same conditions. The invention herein is believed to be the first example of selenoxidation by a specific monooxygenase, namely, dopamine-beta-hydroxylase.

The compounds of this invention, acting as substrates for the enzyme dopamine-beta-hydroxylase, consume two equivalents of ascorbic acid in the normal oxygenation process of dopamine-beta-hydroxylase. However, due to the unusual electrochemical properties of the resultant selenoxide product, spontaneous consumption of additional equivalents of ascorbic acid accompanies the reduction of this selenoxide product back to the original enzyme substrate form (e.g., back to the selenide). Thus, it is suggested that the infusion of a chosen derivative of this invention as the enzyme substrate results in an oxygenation/reduction cycle initiated and sustained by the target enzyme dopamine-beta-hydroxylase, which operates at the expense of intracellular ascorbic acid stores. This process can be used pharmaceutically to inhibit (reversibly) the function of adrenergic neurons in several locations in the body, including the central nervous system, the peripheral nervous system, and the adrenal glands. This result is highly unexpected and appears to result from and be limited to the phenyl selenides of this invention.

The prior art does not teach the aminoalkyl phenyl selenides or pharmaceutically acceptable salts thereof, nor the unexpected depletion of intracellular ascorbic acid which is characteristic of this invention.

BRIEF SUMMARY OF THE INVENTION

Accordingly, it is an object of this invention to provide a new class of compounds suitable for the treatment of hypertension and related vascular diseases, and for the treatment of nervous system dysfunctions by the direct intrinsic activity of these compounds and by the metabolic products of these compounds after enzymatic activation.

Another object of this invention is to provide new compounds which possess a phenyl selenide group located within the drug molecule at a position which makes these molecules possess activity at neurochemical receptors and which makes them effective substrates for a specific oxygenase, dopamine-beta-hydroxylase, which can convert them into selenoxide species capable of gently modifying both neuronal function and cardiovascular tone. The selenide compounds as well as their enzyme products can interact with normal uptake and catabolic pathways to potentiate their effects and to aid in the normal elimination of these compounds from the body.

An important object of this invention is to provide a new class of compounds displaying a new approach to the treatment of the pathologies of the human cardiovascular and nervous system. The intrinsic activities of the phenyl selenides of this invention are potentiated by their enzymatic conversion from relatively inactive pro-drug precursors into highly active enzyme products.

These objects may be attained by treatment of an effective amount of aminoalkyl phenyl selenide derivative having the formula:

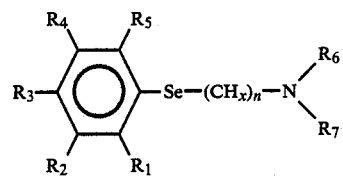

wherein:
$R_1$–$R_7$=H, OH, $C_1$–$C_4$-alkoxy, $C_1$–$C_4$-alkyl, F, Cl, Br, I;

$(CHx)_n$=any straight or branched, saturated or unsaturated alkyl chain of 1 to 10 carbons (x-0,1,2);

and pharmaceutically acceptable addition salts thereof.

BRIEF DESCRIPTION OF THE DRAWING

The FIGURE of the drawing is a graphic depiction of the cyclic path of ascorbate oxidation by the aminoalkyl phenyl selenides of the present invention.

DETAILED DESCRIPTION OF THE INVENTION AND PREFERRED EMBODIMENTS

The compounds used in this invention are in general parallel to the compounds disclosed in the May et al. U.S. Pat. No. 4,415,591 with the important distinction that the phenyl sulfide group of that patent is replaced by the phenyl selenide group of this invention to yield the capability for depletion of intracellular ascorbic acid. Thus, the phenyl ring can be substituted or unsubstituted, and the alkyl moiety between the selenium atom and the amino group may be any linear or branched, saturated or unsaturated chain of 1 to 10 carbons. Suitable substituents $R_1$-$R_7$ include H, OH, $C_1$-$C_4$-alkyl groups, such as methyl, ethyl, n-propyl, isopropyl, n-butyl, isobutyl, secbutyl, and t-butyl; $C_1$-$C_4$-alkoxy groups such as methoxy, ethoxy, n-propoxy, isopropoxy, n-butoxy, isobutoxy, secbutoxy, t-butoxy, hydroxy, and halogen, such as fluorine, chlorine, bromine and iodine. Suitable groups for the alkyl moiety between the selenium atom and the amino group include methylene, ethylene, 1,3-propylene, 1,4-butylene, 1,6-hexylene, octamethylene, decamethylene, 2-methyl-1,3- propylene, 3-methyl-1,5-pentylene, 3-ethyl-1-1,5-pentylene, 2-ethyl-1,6-pentylene, 2-ethyl-1,6-hexylene, 2-ethyl-1,8-octylene, 5-methyl-1,9,nonylene, and the like.

Suitable compounds useful in this invention include phenyl-2-aminoethyl selenide, 2-(methylamino)ethyl phenyl selenide, 2-(dimethylamino)ethyl phenyl selenide, 2-(ethylamino)ethyl phenyl selenide, 2-(n-propylamino)ethyl phenyl selenide, 2-(n-butylamino)ethyl phenyl selenide, 2-aminoethyl 4-hydroxyphenyl selenide, 2-aminoethyl 3,4-dihydroxyphenyl selenide, 2-aminoethyl 3,5-dihydroxyphenyl selenide, 2-aminoethyl 4-methyl phenyl selenide, 2-aminoethyl 2,4-dimethyl phenyl selenide, 2-amino-ethyl 4-ethylphenyl selenide, 2-aminoethyl 4-propylphenyl selenide, 2-aminoethyl 4-butylphenyl selenide, 2-aminoethyl 4-methoxyphenyl selenide, 2-aminoethyl 4-ethoxy phenyl selenide, 2-aminoethyl 4-propoxyphenyl selenide, 2-amino-ethyl 4-butoxyphenyl selenide, 2-aminoethyl 3,4-dimethoxy phenyl selenide, 2-aminoethyl 3,4,5-trimethoxyphenyl selenide, 3-aminopropyl phenyl selenide, 4-aminobutyl phenyl selenide, 6-aminohexyl phenyl selenide, 8-aminooctyl phenyl selenide, 10-aminodecyl phenyl selenide, 6-amino-2-ethylhexyl phenyl selenide, 3-amino-2-methylpropyl 3,4-dihydroxyphenyl selenide, 4-amino-3-methylbutyl 3,4-dimethoxyphenyl selenide, 4-methylamino-3-methylbutyl 3,4-dimethoxyphenyl selenide, and the like.

The compounds used in this invention may also be used in the form of their acid addition salts with non-toxic pharmaceutically acceptable acids. Such salts include the hydrochloride, sulfate, hydrobromide, citrate, acetate, gluconate, and the like.

A preferred compound is phenyl-2-aminoethyl selenide and salts thereof. Phenyl-2-aminoethyl selenide (PAESe) was synthesized by employing the following procedure. Diphenyl diselenide, 24.707 g (79.16 mmol) was dissolved into 100 ml of tetrahydrofuran (THF) with steam heating. To the intensely dark red THF solution was added 9.84 ml (95 mmol, 1.2 eq.) of 50% hypophosphorous acid and the reaction was refluxed under argon for 6 hours, cooled, and diluted with 200 ml of $Et_2O$ and washed with 200 ml of 0.127M NaOAc buffer pH 5.0 to remove the phosphoric acid by-product. Both the $Et_2O$ and the buffer were deoxygenated by bubbling argon through fritted glass for over 1 hour in order to prevent reoxidation of phenylselenol to diphenyl diselenide. The washed organic phase was then concentrated to yield a yellow oil (diselenide contaminant) with residual salt-containing water pockets. The crude product was pumped down to remove residual solvent prior to distillation, which yielded the desired phenylselenol (12.6 g, 51% yield). pNMR (CDCl$_3$) (s, 1H) 1.54 d (m, 5H) 7.35 d. Yields as high as 70% have been obtained for this reaction.

The phenylselenol obtained was refluxed under argon overnight with 7.5 ml (88.45 ml, 1.1 eq.) of 2-methyl-2-oxazoline and 3 ml of benzene. Upon cooling, the entire reaction solidified to a dense pale yellow solid which was recrystallized from benzene to yield 18.076 g (74.63 mmol, 92.8% yield) of N-acetyl-phenyl-aminoethyl selenide as shiny white plates. pNMR (CDCl$_3$) (s, 3H) 1.90 d, (m, 2H) 3.08 d, (m, 2H) 3.57 d J=6 Hz, (broad s, 1H) 6.11 d, (m, 5h) 7.48 d. mass spec (m/e 243 molecular ion).

The acetamide was hydrolyzed by refluxing overnight in 100 ml of 6M HCl. The solution was then cooled in an ice bath and basified to pH 13 by the slow addition of solid NaOH, extracted with four 25 ml portions of CHCl$_3$, and the combined chloroform extracts were dried over anhydrous $K_2CO_3$, filtered, and the solvent removed in vacuo to yield 15.680 g of the free amine (plus residual CHCl$_3$) as a clear yellow liquid. The hydrochloride salt was obtained by the addition of 6.5 ml of 12M HCl (1.05 eq) to 60 ml of a EtOH/$Et_2O$ (2:1) solution of the free amine. Recrystalization from EtOH/$Et_2O$ (2:1) yielded the final product; mp 149.2°–150.7° C., loss of crystal structure at 131° C.; pNMR (D$_2$O) (s, 4H) 3.21 d, (m, 5H) 7.58 d; mass spec (m/e 201 molecular ion); elemental analysis for $C_8H_{12}ClNSe$ THEORY C 40.61, H 5.12, N 5.92 FOUND C 40.73, H 5.11, N 5.90.

Other aminoalkyl phenyl selenides of the present invention can be synthesized by generally following the above procedure. For compounds in which $R_6$ or $R_7$ are those other than H or acetoxy, the preparation of such compounds involves the synthesis of the appropriately substituted halogenated side chain by standard methods and subsequent nucleophilic attack by the chosen selenide precursor, with appropriate blocking procedures familiar to those skilled in the art.

When compounds of this invention are used as antihypertensive compounds, they may be administered orally, parenterally or rectally and may be formulated in compositions and dosage forms for such administration. In these compositions and dosage forms the compounds are admixed with conventional nontoxic pharmaceutical excipients. Solid dosage forms for oral administration include capsules, tablets, pills, powders, and granules. In such solid dosage forms, the active compound is admixed with at least one inert diluent such as sucrose, lactose, or starch. Such dosage forms can also comprise, as is normal practice, additional substances other than inert diluents, e.g., lubricating agents such as magnesium stearate. In the case of capsules, tablets, and pills, the dosage forms may also comprise buffering agents. Tablets and pills can also be prepared with an enteric coating.

Liquid dosage forms for oral administration include pharmaceutically acceptable emulsions, solutions, suspensions, syrups, and elixirs containing inert diluents commonly used in the art, such as purified water and alcohols. Besides inert diluents, such compositions can also include adjuvants, such as wetting agents, emulsifying and suspending agents, and sweetening, flavoring, and perfuming agents. Preparations according to this invention for parenteral administration include sterile aqueous or nonaqueous solutions, suspension or emulsions. Examples of nonaqueous solvents or vehicles are propylene glycol, polyethylene glycol, vegetable oils such as olive oil and injectable organic esters such as ethyl oleate.

Compositions for rectal administration are suppositories which may contain in addition to the active substance, excipients such as cocoa butter or a suppository wax.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.5 to 100 mg/kg of body weight daily are administered to mammals to obtain effective relief of hypertension. A preferred dosage level is 1.0 to 50.0 mg/kg of body weight. The reduction of blood pressure varies with dosage levels.

The hydrochloride salt of phenyl-2-aminoethyl selenide was administered in a commonly-used model of human hypertension, the spontaneously hypertensive rat (SHR). In a series of experiments, the compound when administered in doses ranging to 100 mg/kg, it was demonstrated as very potent in lowering blood pressure of SHR and the aforesaid variation with dosage levels was also demonstrated. When one group of SHR was administered intraperitonally with the compound in a saline carrier at a dosage of 50 mg/kg and a control group was administered only with the saline carrier, a decrease in systemic blood pressure of approximately 30% in comparison with the control animals was observed. In addition, no adverse side effects from the chronic administration of the compound were observed when given in daily dosages over a two week period, while substantial blood pressure reduction was maintained. See Example 2 below.

In treating hypertension in mammals by the method of this invention, it may not be necessary to administer the aminoalkyl phenyl selenide in combination with a monoamine oxidase inhibitor, which would have the effect of prolonging life of the active compounds in the body. It has been found that when the $(CH_x)_n$ substituent of the compounds of the present invention is a branched alkyl chain of ten carbons or less, the resulting aminoalkyl phenyl selenide is a relatively inactive prodrug precursor which is potentiated by its enzymatic conversion into a highly active enzyme product. Thus, a monoamine oxidase inhibitor may not be desirable in the administration of such "branched" aminoalkyl phenyl selenides.

On the other hand, it has been found that compounds having a straight chain or "nonbranched" $(CH_x)_n$ substituent are relatively active, and may be potentiated by the co-administration of such "nonbranched" aminoalkyl phenyl selenides in combination with a monoamine oxidase inhibitor. The combination of aminoalkyl phenyl selenide derivatives and monoamine oxidase inhibitors such as clorgyline, deprenyl, nardil (phenethylhydrazine sulfate) or others currently in clinical use may protect the selenide or selenoxide product and therefore allow a longer active period in the body, resulting in an increased anti-hypertensive effect.

Although the exact mechanism by which the compounds used in the process of this invention exert their physiological effect is uncertain, and applicants do not wish to be bound by any theoretical consideration, it is possible that the unique biochemical action, i.e. reduction/oxidation properties of these compounds, may play a part in their activity alone or in combination with their action as false neurotransmitters as described in the May et al. U.S. Pat. No. 4,415,591. Other mechanisms related to neuronal uptake and regulation of enzymatic activities may also be involved in the activities of the compounds.

The effectiveness of the compounds used in the process of this invention as anti-hypertensive agents can be evaluated by an enzymatic oxygenation process as disclosed in the aforesaid May et al. U.S. Pat. No. 4,415,591, the subject matter of which is incorporated herein by reference. Using the standard substrate 2-phenylethylamine, the carbon analog 3-phenylpropylamine and the substrate phenyl-2-aminoethyl selenide of this invention with ascorbic acid as the electron donor, the values of $k_{cat}$, and $k_{cat}/K_m$ using 300 micrograms per milliliter of catalase were $48s^{-1}$ and $2.9 \times 10^3 M^{-1}s^{-1}$, respectively.

As noted above, the enzymatic oxygenation products of the compounds of this invention possess unusual electro-chemical properties such that a unique aspect of the dopamine-beta-hydroxylase (DBH) catalyzed oxygenation of aminoalkyl phenyl selenides to the corresponding selenoxides is the ability of the selenoxides to oxidize the physiological electron donor, ascorbate, with the concomittant and stoichiometric reduction of the selenoxides back to the selenide substrate. The oxygenation of aminoalkyl phenyl selenide by DBH and the reduction of the enzymatic product, aminoalkyl phenyl selenoxide back to the selenide by ascorbate defines a cyclic path of ascorbate oxidation where an excess of ascorbate is oxidized per cycle, as illustrated in the Figure of the drawing. Thus, when compounds of this invention are infused, it is likely that an enzymatic oxygenation/reduction cycle is initiated and sustained by the target enzyme dopamine-beta-hydroxylase.

EXAMPLE 1

The ability of phenyl-2 aminoethyl selenoxide (PAESeO) to oxidize ascorbate was explored. High pressure liquid chromatography (HPLC) was used to show that the authentic selenoxide was stable at room temperature in the standard dopamine-beta-hydroxylase (DBH) reaction mixture which did not contain ascorbate. Upon the addition of ascorbate to a final concentration of 10 mM, PAESeO disappeared from the HPLC chromatogram and a peak with the same retention time as phenyl-2 aminoethyl selenide (PAESe) appeared. As can be seen in Table I when a mixture of 10 mM PAESeO and 5 mM ascorbate in water was allowed to react for 24 minutes at room temperature, HPLC analysis demonstrated that the concentration of PAESeO was diminished by 50% at the expense of ascorbate and that a corresponding amount of PAESe was formed. Similarly, the reaction of 10 mM PAESeO and 10 mM ascorbate for 60 minutes resulted in the complete depletion of the selenoxide and the appearance of a PAESe peak, the height of which correspond to 9.2 mM PAESe. These results demonstrate that PAESeO is stoichiometrically reduced to PAESe by ascorbate. In contrast to the reduction of PAESeO by ascorbate, the reaction of 10 mM PAESeO and 10 mM potassium ferrocyanide for 64 minutes did not result in the appearance of any PAESe or the loss of any PAESeO.

TABLE I

STOICHIOMETRIC REDUCTION OF SELENOXIDE TO SELENIDE BY ASCORBATE

| EXP # | Initial Composition of Reaction Mixture | Final Reaction Products Determined By High Pressure Liquid Chromatography | |
|---|---|---|---|
| | | PAESeO (mM) | PAESe (mM) |
| 1 | 10 mM PAESeO 10 mM Reduced Ascorbate | 0 | 9.2 |
| 2 | 10 mM PAESeO 5 mM Reduced Ascrobate | 5.2 | 5.1 |
| 3 | 15 mM PAESeO 5 mM Reduced Ascorbate | 9.9 | 4.7 |

EXAMPLE 2

The antihypertensive activity of 1-phenyl-2-aminoethyl selenide (PAESe) was demonstrated in the following experiment. Ten male spontaneously hypertensive rats (SHR), at 13 weeks of age, were obtained from Charles River Breeding Laboratories, Inc. SHR of the Okamoto-Aoki strain are an inbred rat strain derived from a mutant progenitor in which the defect which produces hypertension has been shown to be essential, i.e., not renal hypertension (see Bey, P., Jung, M. J., and Loch-Weser, J., (1980) *Brit. J. Pharmacol.* 70, 571–576; Judy, W. V., Watanabe, A. M., Henry, D. P., Besch, H. R., Murphy, W. R., and Hockei, G. M., (1976) *Circ. Res.* 38, Suppl. I: 21–29; and references in these for more detail). Thus, this model of essential hypertension is an ideal one in which to test drugs for antihypertensive activity for eventual use in the treatment of human essential hypertension.

The animals were housed for several weeks in an approved caging facility, allowed food and water ad libitum, and acclimated in 5–10 trials to an indirect systolic blood pressure monitoring protocol (tail-cuff plethysmographic measurement, Narco BioSystem, Inc.). The animals were divided into two groups of five and received either 50 mg/kg PAESe or saline, (1 ml/kg) by subcutaneous injection at 24 hour intervals for seven consecutive days. Systolic blood pressure monitoring was performed using the indirect tail cuff method at one hour and three hours post-injection on each of the seven days. This testing revealed a significant 30% reduction in the blood pressure of the PAESe-treated group, apparent after the initial 24 hours post-injection, and maintained for seven days.

In these experiments, the test animals were conscious at all times during the experimentation, betrayed no behavioral changes as a result of the drug treatment, and sustained no weight losses as a result of the treatment. Additionally, we have found that PAESe is nontoxic in this animal model up to the highest levels tested so far, and that its blood pressure-lowering effects are reversible. That is, in animals who have received PAESe over a 3–7 day period at 24 hour intervals, withdrawal of this compound is marked by a return of the animal's blood pressure to the normal hypertensive levels, suggesting the PAESe is catabolized and eliminated by one of the normal physiological drug elimination pathways.

Having now fully described the invention, it will be apparent to one of ordinary skill in the art that many changes and modifications can be made thereto without departing from the spirit or scope of the invention as set forth herein.

What is claimed is:

1. A method for depleting intracellular ascorbic acid in mammals comprising administering to the mammal an amount of an aminoalkyl phenyl selenide effective to initiate an oxidation/reduction cycle which is sustained by the target enzyme dopamine-beta-hydroxylase having the formula:

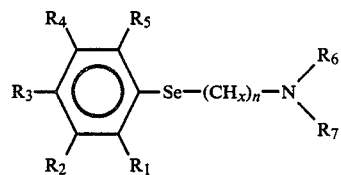

wherein:
$R_1$–$R_5$=H, OH, $C_1$–$C_4$-alkoxy, $C_1$–$C_4$-alkyl, F, Cl, Br, or I;
$R_6$, $R_7$=H, $C_1$–$C_4$-alkyl; and
$(CH_x)_n$=any straight or branched, saturated or unsaturated alkyl chain of 10 carbons or less, n=1 to 10 carbons and x=0, 1, or 2 hydrogens; or a pharmaceutically acceptable salt thereof.

2. The method as defined in claim 1 wherein the aminoalkyl phenyl selenide is phenyl-2-aminoethyl selenide.

3. The method as defined in claim 1 wherein said amount is 1–50 mg/kg of body weight of the mammal.

4. A pharmaceutical composition comprising an aminoalkyl phenyl selenide compound having the formula:

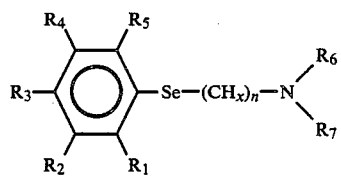

wherein:
$R_1$–$R_5$=H, OH, $C_1$–$C_4$-alkoxy, $C_1$–$C_4$-alkyl, F, Cl, Br, or I;
$R_6$, $R_7$=H, $C_1$–$C_4$-alkyl; and
$(CH_x)_n$=any straight or branched, saturated or unsaturated alkyl chain of 10 carbons or less, n=1 to 10 carbons and x=0, 1, or 2 hydrogens; and a pharmaceutically acceptable nontoxic excipient, said selenide compound being present in an amount effective to deplete intracellular ascorbic acid in mammals by initiating an oxidation/reduction cycle which is sustained by the target enzyme dopamine-beta-hydroxylase.

5. The method of claim 1 wherein the aminoalkyl phenyl selenide compound is administered in combination with a clinically utilized monamine oxidase inhibitor, said inhibitor being selected from the group consisting of clorgyline, deprenyl and nardil.

* * * * *